United States Patent
Saleh et al.

(10) Patent No.: US 8,807,390 B2
(45) Date of Patent: Aug. 19, 2014

(54) INDICATION SEQUENCE FOR ENERGY EFFICIENT VOLATILE MATERIAL DISPENSERS

(71) Applicants: Saleh A. Saleh, Vernon Hills, IL (US); Gene Sipinski, Elgin, IL (US); Craig J. Witcraft, Vernon Hills, IL (US)

(72) Inventors: Saleh A. Saleh, Vernon Hills, IL (US); Gene Sipinski, Elgin, IL (US); Craig J. Witcraft, Vernon Hills, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 52 days.

(21) Appl. No.: 13/658,569

(22) Filed: Oct. 23, 2012

(65) Prior Publication Data
US 2014/0110428 A1 Apr. 24, 2014

(51) Int. Cl.
- B67D 7/06 (2010.01)
- B65D 83/00 (2006.01)
- A61L 9/14 (2006.01)

(52) U.S. Cl.
CPC . *B65D 83/00* (2013.01); *A61L 9/14* (2013.01); *A61L 2209/11* (2013.01)
USPC ............... 222/23; 222/63; 222/183; 222/325; 222/504; 222/648; 239/69

(58) Field of Classification Search
USPC ............ 239/67–70; 222/23, 39, 63, 182–183, 222/325, 504, 644–649
See application file for complete search history.

(56) References Cited

U.S. PATENT DOCUMENTS

| | | |
|---|---|---|
| D244,200 S | 5/1977 | Ramos et al. |
| 5,038,972 A * | 8/1991 | Muderlak et al. ............... 222/25 |
| 5,111,477 A | 5/1992 | Muderlak et al. |
| 5,175,791 A | 12/1992 | Muderlak et al. |
| RE34,847 E | 2/1995 | Muderlak et al. |
| 5,908,140 A * | 6/1999 | Muderlak et al. .................. 222/1 |
| 6,394,310 B1 | 5/2002 | Muderlak et al. |
| 6,644,507 B2 | 11/2003 | Borut et al. |
| 6,769,580 B2 * | 8/2004 | Muderlak et al. ............ 222/646 |
| 6,877,636 B2 | 4/2005 | Speckhart et al. |
| 7,832,655 B2 | 11/2010 | Tollens et al. |
| 8,070,139 B2 | 12/2011 | Nassirpour et al. |
| 2007/0199952 A1* | 8/2007 | Carpenter et al. ............... 222/52 |
| 2007/0235555 A1 | 10/2007 | Helf et al. |
| 2008/0011874 A1 | 1/2008 | Munagavalasa et al. |
| 2008/0290113 A1 | 11/2008 | Helf et al. |
| 2009/0185958 A1* | 7/2009 | Nassirpour et al. ........... 422/105 |
| 2009/0309717 A1 | 12/2009 | Sipinski et al. |
| 2010/0320227 A1* | 12/2010 | Reynolds ......................... 222/52 |
| 2011/0076185 A1 | 3/2011 | Hammond et al. |
| 2011/0284653 A1 | 11/2011 | Butler et al. |
| 2012/0024975 A1 | 2/2012 | Sharma et al. |
| 2012/0091219 A1 | 4/2012 | Sipinski et al. |

FOREIGN PATENT DOCUMENTS

EP 1214949 6/2002

OTHER PUBLICATIONS

PCT/US2013/065585 International Search Report and Written Opinion dated Feb. 24, 2014.

* cited by examiner

*Primary Examiner* — Paul R Durand
*Assistant Examiner* — Andrew P Bainbridge

(57) ABSTRACT

An energy efficient dispenser for dispensing product from a container includes at least one indicator for displaying a first indication sequence when the dispenser is in a dispense mode operational state and a second indication sequence when the dispenser in a lockout mode operational state. Each indication sequence includes one or more activations of the at least one indicator, which utilize no more than 0.0625 mAh of energy to provide an indication to a user of the operational state of the dispenser.

20 Claims, 4 Drawing Sheets

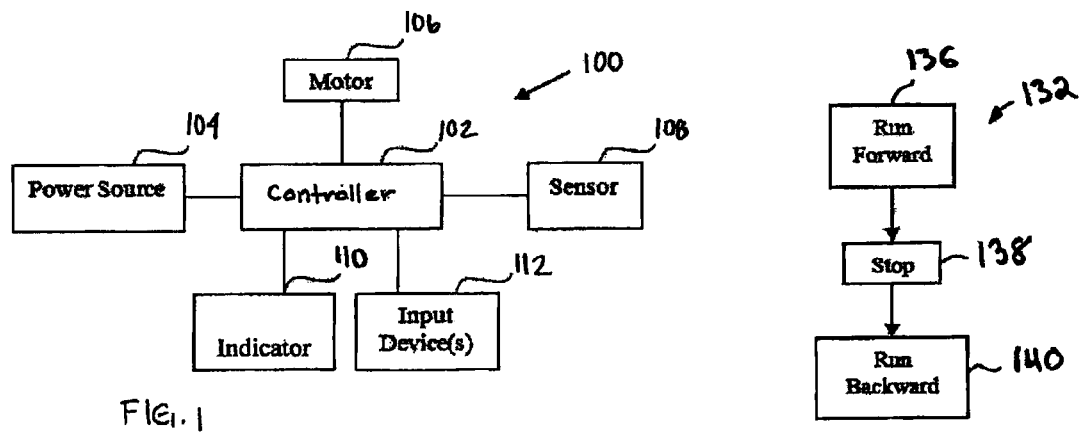
FIG. 1
FIG. 3
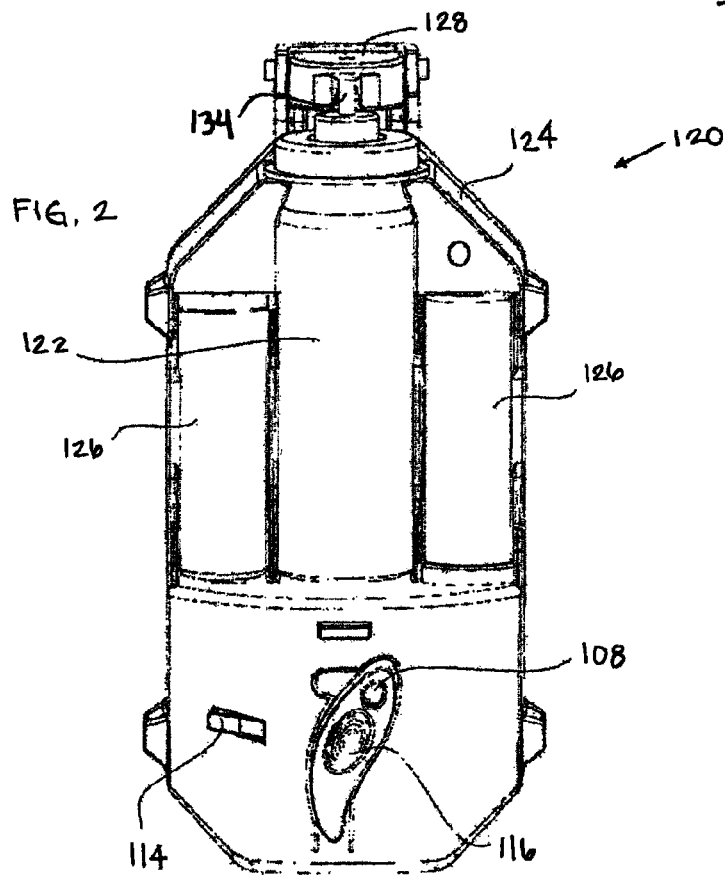
FIG. 2
(PRIOR ART)

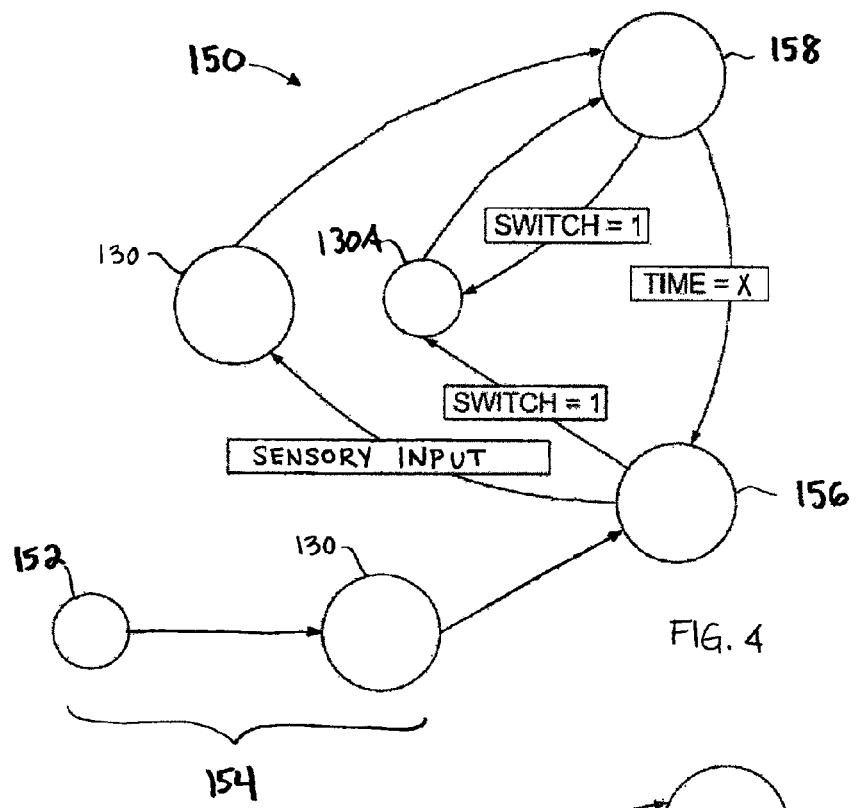
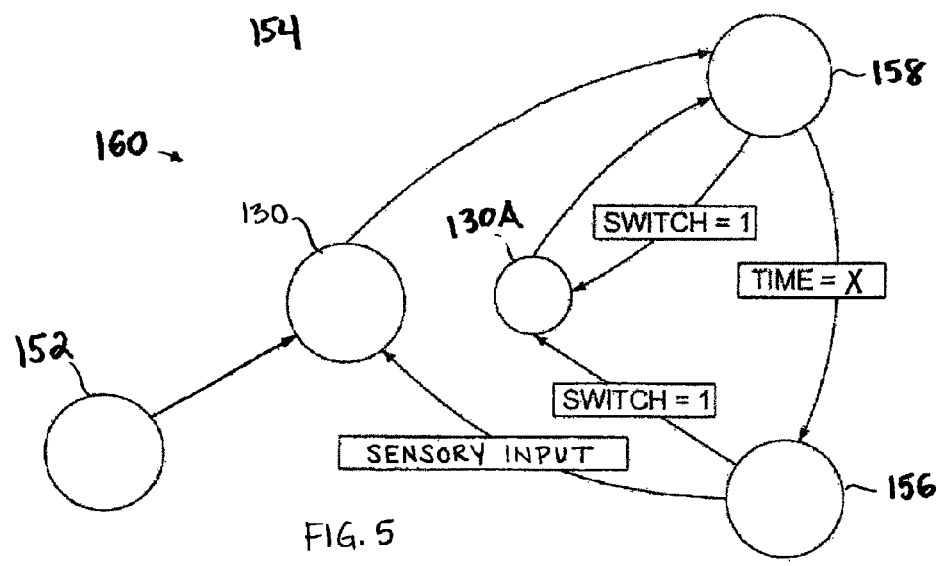
FIG. 4
FIG. 5

INDICATION SEQUENCE FOR ENERGY EFFICIENT VOLATILE MATERIAL DISPENSERS

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to an energy efficient dispenser having an indication sequence that informs a user of the state of the dispenser and methods of operating same.

2. Description of the Background of the Invention

Diffusion devices or dispensers are used to dispense volatile materials, such as fragrances, deodorizers, insecticides, insect repellants, and the like. Many of these dispensers are active dispensers, which may include fans and/or heaters to aid in the dispersal of volatile materials, others actuate a valve stem of an aerosol container to dispense a volatile material contained therein, still others utilize an ultrasonic transducer to break up a liquid volatile material into droplets that are ejected from the device, and yet others include any combination of the above or any other known type of active diffusion device.

Traditionally, these active dispensers include a controller that implements an operational methodology to release the volatile material from the dispenser. The volatile material is often released in response to input from a sensor, the depression of a pushbutton, or upon lapsing of a time interval. The operating methodologies also often include periods that the volatile material is prevented from being released and/or periods that a sensor is inactive. In order to inform a user of the operational state of the dispenser, many dispensers include an audible indicator or a visual indicator, such as an LED which blinks according to an LED indication sequence. The drawback of traditional LED indication sequences is that they consume excessive amounts of power.

Recently, consumers have become more conscious of the amount of energy they consume in their daily lives. Many consumers are surprised to learn that powering an LED according to a traditional operational sequence often consumes more energy than powering the dispenser to release the volatile material itself. Consumers are therefore desirous of limiting the amount of energy they use. Thus, it would be beneficial to create a dispenser, which uses less energy to operate than traditional dispensers. Such energy efficient dispensers that utilize batteries as a power source will have the added benefit of allowing a user to replace the batteries less frequently, which is more convenient to a user and less expensive.

Consequently, a need has arisen for energy efficient dispensers that provide the user an indication of the operational state of the dispenser using various patterned indication sequences. The present disclosure relates to solutions to address such needs.

SUMMARY OF THE INVENTION

According to one embodiment, an energy efficient dispenser for dispensing product from a container includes at least one indicator for displaying a first indication sequence when the dispenser is in a dispense mode operational state and a second indication sequence when the dispenser is in a lockout mode operational state. Each indication sequence includes one or more activations of the at least one indicator, which utilize no more than 0.0625 mAh of energy to provide an indication to a user of the operational state of the dispenser.

According to a different embodiment, an energy efficient dispenser for dispensing product from a container includes at least one indicator for providing one or more indication sequences. Each indication sequence includes one or more activations of the at least one indicator, which utilize no more than 0.0625 mAh of energy and operate using a pulse width mode of operation at a duty cycle of about 40% to about 80% to provide an indication to a user of the operational state of the dispenser. The operational state includes at least one of an active mode, a dispense mode, and a lockout mode.

According to a further embodiment, an energy efficient dispenser includes a housing for receipt of a container and one or more batteries having a capacity rating of about 400 mAh to about 4000 mAh. The dispenser further includes at least one of a timer and a sensor adapted to detect sensory input. The dispenser also includes at least one indicator. The at least one indicator provides one or more indication sequences, wherein each indication sequence includes one or more activations of the at least one indicator to provide an indication to a user of the operational state of the dispenser. Further, the batteries are capable of providing power to the dispenser for at least seven months of continuous operation of the dispenser.

According to a still further embodiment, a method of operating an energy efficient dispenser includes the steps of applying a power source to a dispenser and entering an operational state, which includes one of a startup procedure, a dispense mode, and a lockout mode. The method further includes the step of performing an indication sequence, which includes performing one or more activations of at least one indicator to provide an indication to the user of the operational state of the dispenser. Activation of the visual indicator utilizes no more than 0.0625 mAh of energy.

Other aspects and advantages of the present invention will become apparent upon consideration of the following detailed description.

BRIEF DESCRIPTION OF THE DRAWINGS

FIG. 1 is a block diagram of one embodiment of a dispenser;

FIG. 2 is an isometric view of a dispenser according to another embodiment;

FIG. 3 is a flowchart that illustrates programming for a release operation that may be executed by the dispensers of FIGS. 1 and/or 2;

FIG. 4 is a flowchart that illustrates an operational procedure that may be executed when a power source is applied to the dispensers of FIGS. 1 and/or 2;

FIG. 5 is a flowchart that illustrates another embodiment of an operational procedure that may be executed when a power source is applied to the dispensers of FIGS. 1 and/or 2;

DETAILED DESCRIPTION OF THE DRAWINGS

Figure 6A:
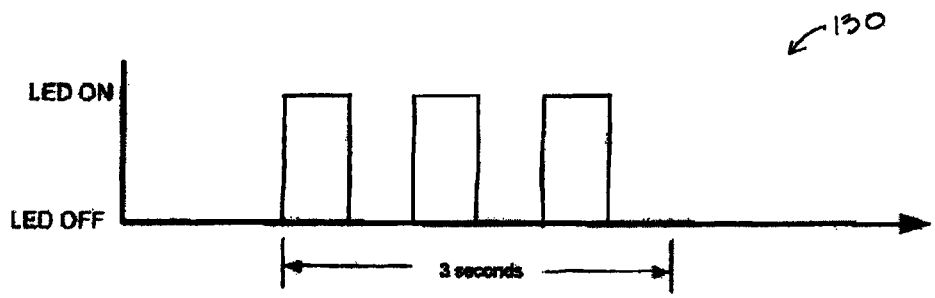
FIG. 6A is a chart that illustrates a prior art LED indication sequence that may be executed during a dispense mode of the operational procedure of FIGS. 4 and/or 5.

FIG. 1 illustrates a device 100 that includes a controller 102, a power source 104, a motor 106, a sensor 108, a timer (not shown), and an indicator 110, e.g., a light emitting diode ("LED"). The device may also include one or more input devices 112 such as switches, dials, keypads, pushbuttons, etc. An example of the input device 112 may be a switch 114 (see FIG. 2), which allows the user to turn on the device 100 and/or a pushbutton 116, which allows the user to initiate a dispense mode, e.g., a spray operation. The power source 104 supplies power to the controller 102 and to the other components, wherein the controller 102 is further coupled to the other components and executes programming to control the operation thereof.

FIG. 2 illustrates one embodiment of the device 100 of FIG. 1 implemented as a dispenser 120 for dispensing the contents of an aerosol container 122, which may include any fluid, volatile material, or product known to those of skill in the art. The dispenser 120 may be one of the devices described in Carpenter et al. U.S. patent application Ser. No. 11/725, 402, Furner et al. U.S. patent application Ser. No. 13/302,911, Gasper et al. U.S. patent application Ser. No. 13/607,581, and Baranowski et al. U.S. patent application Ser. No. 13/607, 581. The dispenser 120 includes a housing 124 that is adapted to receive the aerosol container 122 and batteries 126. The housing 124 also includes an actuator arm 128, the selector switch 114, and the pushbutton 116. In addition, the dispenser 120 also includes circuitry, the controller 102, the motor 106, and the sensor 108, which are provided within the housing 124 and shown generally in FIG. 1.

The sensor 108 in the present embodiment may be a photocell light sensor. In one embodiment, changes in the detected level of light by the sensor may be construed as detected motion. The sensor 108 may be the sensor described in Carpenter et al. U.S. patent application Ser. No. 11/725, 402. However, any other type of detector or sensor may be utilized for detecting sensory input, e.g., a passive infrared or pyroelectric motion sensor, an infrared reflective motion sensor, an ultrasonic motion sensor, or a radar or microwave radio motion sensor. Further, the sensor 108 can be replaced or used in combination with any other type of known sensor such as an accelerometer or acoustic, humidity, temperature, pressure, vibration, or chemical (e.g. scent) sensor. Still further, the sensor does not have to be located within the housing 124 of the dispenser 120; rather, the sensor 108 can be a remote sensor for detecting motion or some other sensory input. Additionally, the sensor could comprise a mechanical contact switch internal to the housing, or located externally from the housing, which is responsive to physical contact to indicate sensory input.

The controller 102 controls the motor 106 during a dispense mode operational state 130 to perform a spray operation 132. During the spray operation 132, the motor 106 actuates the actuator arm 128, which depresses a valve stem 134 of the aerosol container 122 to dispense the contents therefrom. The controller 102 includes programming to initiate the dispense mode 130 to perform the spray operation 132, in response to a signal generated from the sensor 108. Alternatively, or in conjunction with signal initiated actuation, the controller 102 could initiate a dispense mode 130 in response to a signal generated by a switch, a pushbutton, and/or a timer.

FIG. 3 illustrates the spray operation 132 of the present embodiment. The spray operation 132 begins at the block 136 where the motor 106 is energized to move the actuator arm 128 to cause the depression or actuation of the valve stem 134 of the aerosol container 122 into an open position. The motor 106 is deenergized and stopped in block 138. Thereafter, the motor 106 is energized to move the actuator arm 128 in the opposite direction in block 140 to assist the valve stem 132 in moving to a closed and non-depressed position. In the present embodiment, the length of time the motor 106 is energized to move the actuator arm 128, as indicated in block 136, is preferably between about 800 milliseconds to about 1200 milliseconds and most preferably 1000 milliseconds, the length of time the motor 106 is stopped (block 138) is preferably between about 100 milliseconds to about 200 milliseconds and most preferably 150 milliseconds, and the length of time the motor 106 is energized to move the actuator arm in the opposite direction (block 140) is preferably between about 200 milliseconds to about milliseconds 600 and most preferably 400 milliseconds. However, the length of time the motor is energized or deenergized may be changed to effect the volume of spray released. Thus, the dispenser 120 can be programmed to release any volume of spray from the container 122 by merely changing the time the motor 106 is energized and/or deenergized. In an alternative embodiment, the valve of the container 122 is metered to emit a predetermined volume of fluid that is independent of the length of time the motor 106 is stopped. Modifications to the spray operation 132 of the present embodiment can include any sequence of the same or different steps, as would be apparent to one of ordinary skill in the art.

FIG. 4, illustrates an embodiment of an operational methodology 150 executed by the dispenser 120. The operational methodology 150 is implemented at initiate mode block 152 when power is supplied to the controller 102. Power is supplied to the controller 102 when the selector switch 114 is toggled into an on position. Alternatively, if the selector switch 114 is not provided, the initiate mode block 152 may be responsive to the insertion of the batteries 126 into the dispenser 120 or the provision of some other power source 104 to the dispenser 120, such as plugging the dispenser 120 into a power outlet. A startup procedure 154 is performed following the initiate mode 152. During the startup procedure 154 the dispenser enters the dispense mode operation 130, during which a spray operation is performed, after which the dispenser 120 enters an active mode 156 operational state. In this embodiment, during the initiate mode 152 the LED 110 is powered on for 4.5 seconds prior to the dispenser 120 entering the dispense mode operation 130. It is contemplated that the startup procedure 154 may include any combination of dispense mode operational states 130 to perform spray operations 132, which in some instances may allow the user to determine that the dispenser 120 is functioning properly, e.g., that all of the components are properly coupled together and functioning and that the contents of the container 122 are not depleted. In some embodiments, the sensor 108 may be activated during the initiate mode 152 and utilized during the startup procedure 154. Alternatively, the startup procedure 154 may be omitted entirely.

Still referring to FIG. 4, after the startup procedure 154 the dispenser 120 enters the active mode 156. During the active mode 156, the sensor 108 is enabled and the dispenser 120 performs a sensing operation to detect sensory input as objects or persons pass through the sensor's 108 field of view. Control remains in the active mode block 156 until sensory input is detected, whereupon control passes to block 130 and the dispense mode 130 is performed, during which material is released from the container 122. Upon completion of the dispense mode 130 the dispenser 120 enters a lockout mode 158 operational state, wherein the sensor 108 is deactivated, e.g., by ignoring the output from the sensor 108 or by removing power from the sensor 108, and the dispenser 120 does not enter the dispense mode 130 to perform a spray operation 132 in response to the presence of sensory input. Control remains in the lockout mode block 158 for a certain lockout time period X. When the timer indicates that the lockout time period X has lapsed, control passes back to the active mode block 156 and the sensor 108 is reactivated to detect the presence of sensory input or the output from the sensor 108 is otherwise received and acted upon by the controller 102. In a preferred embodiment, the lockout time period X has a duration of between about 1 to about 180 minutes, or between about 10 to about 60 minutes, or between about 15 to about 40 minutes. In another preferred embodiment, the period X has a duration of between about 15 to about 30 minutes, and more preferably about 20 minutes. In some embodiments, a user can use an input device 112 to select the length of the lockout time period X. For example, in one embodiment, a three position switch (not shown) is used to select between 15, 20, and 30 minute lockout time periods X, though other time periods may be used. At any time a user can depress the pushbutton 116, which causes the dispenser 120 to perform a dispense mode operational state 130A. Upon completion of the dispense mode 130A control passes back to the lockout mode block 158 and the lockout time period X is reset.

Referring now to FIG. 5, another embodiment of an operational methodology 160 is shown, in which the startup procedure is omitted and the operating methodology 160 begins with the initiate mode at block 152. During the initiate mode 152, the LED 110 is powered on for the duration of the initiate mode 152 to illustrate to a user that power is supplied to the dispenser 120 and the dispenser 120 is operational. In the present embodiment, the LED 110 is powered for 19.5 seconds during the initiate mode 152. In other embodiments, the time period is less than 19.5 seconds or greater than 19.5 seconds. After the initiate mode block 152, control passes to block 130 and the dispense mode 130 is performed, in which material is released from the container 122. Upon completion of the dispense mode 130 control passes directly to block 158 and a lockout mode is performed for a lockout time period X. After expiration of the lockout time period X, the dispenser enters an active mode 156. Upon detection of the presence of sensory input by the sensor 108, the dispenser 120 enters the dispense mode 130, a spray operation 132 is performed, and the dispenser 120 thereafter enters the lockout mode 158. At any time the user can press the pushbutton 116, which causes the dispenser 120 to enter a dispense mode 130A and perform a spray operation 132A. Following the dispense mode 130A the lockout time period X is reset and the dispenser 120 reenters the lockout mode 158.

In an alternative embodiment of the operational methodology, the dispenser 120 does not enter the active mode 156 after the lockout mode 158. Rather, upon indication from the timer that the lockout time period X has expired the dispenser 120 immediately enters the dispense mode operational state 130 and product is released from the container. After the dispense mode operational state 130, the dispenser reenters the lockout mode 158 operational state.

Figure 6B:
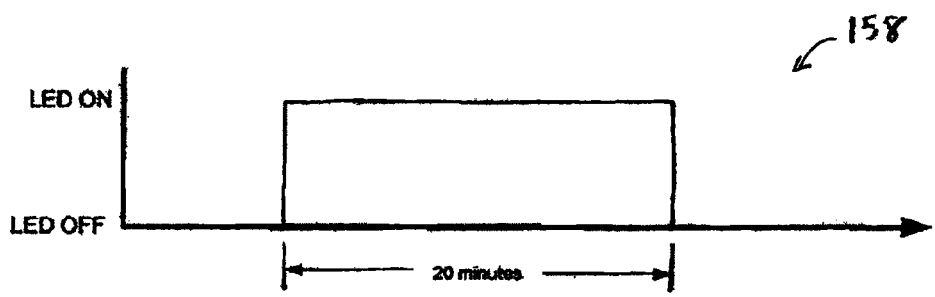
FIG. 6B is a chart that illustrates a prior art LED indication sequence that may be executed during a lockout mode of the operational procedure of FIGS. 4 and/or 5.
Figure 6C:
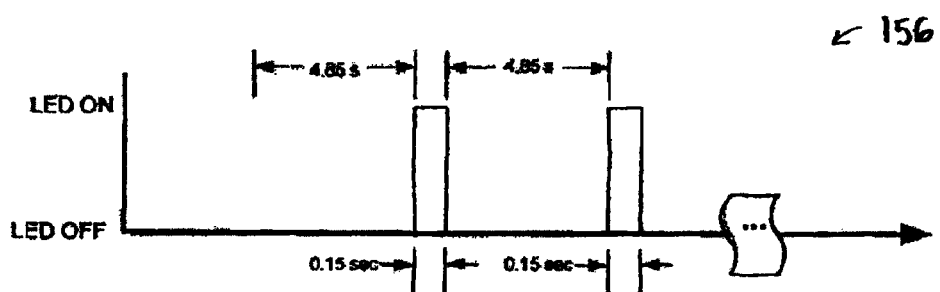
FIG. 6C is a chart that illustrates a prior art LED indication sequence that may be executed during an active mode of the operational procedure of FIGS. 4 and/or 5.

The controller 102 also operates the LED 110 based on an LED indication sequence. The controller operates the LED 110 to indicate to a user the operational state of the dispenser, i.e., the initiate mode 152, the active mode 156, the lockout mode 158, or the dispense mode 130. FIGS. 6A-C illustrate several prior art LED indication sequences. In prior dispensers, the controller activates the LED 110 to blink on and off a predetermined number of times during a dispense mode operational state 130 prior to performing a spray operation 132. For example, FIG. 6A illustrates the controller turning the LED 110 on for 500 milliseconds, and then off for 500 milliseconds, and repeats the sequence for a total of three on/off cycles during a spray operation. As shown in FIG. 6B, during the lockout mode 158 the controller turns the LED on for the full lockout time period X, e.g., 20 minutes. Finally, FIG. 6C illustrates the active mode 156, in which the controller of a prior art device turns the LED off for a 4.85 second interval and then turns the LED 110 on for a successive 0.15 second interval. The controller of this embodiment continues turning the LED 110 on and off until the sensor 108 detects sensory input.

Although the prior art LED indication sequences indicate to users the present operational state of the dispenser, powering the LED 110 according to these lighting sequences requires a considerable amount of energy. For example, in the previously discussed example illustrated by FIGS. 6A-6C, 0.00125 mAH is required to power the LED during the dispense mode operational state 130, 1.000 mAh is required to power the LED during the lockout mode 158, and 0.000486 mAh is required to power the LED 110 during every 5 seconds of the active mode 156. In fact, powering the LED 110 during the 20-minute lockout period requires four times the amount of energy required to power the motor 106 during the dispense mode 130. As such, the LED indicator is a significant factor impacting the energy consumption of the dispenser 120.

Figure 7A:
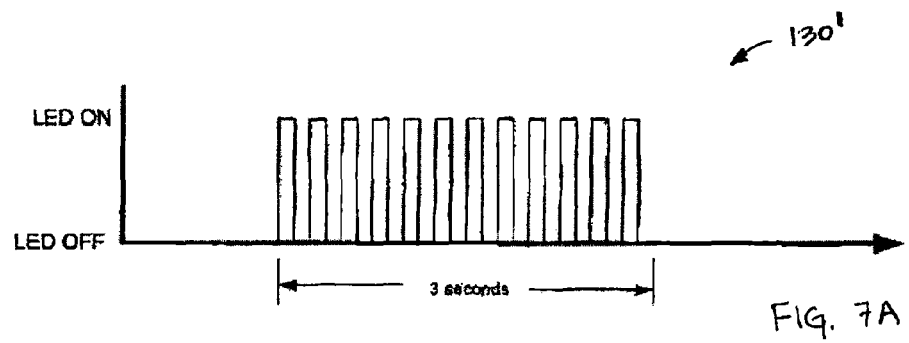
FIG. 7A is a chart that illustrates an LED indication sequence of the present embodiment that may be executed during a dispense mode of the operational procedure of FIGS. 4 and/or 5.
Figure 7B:
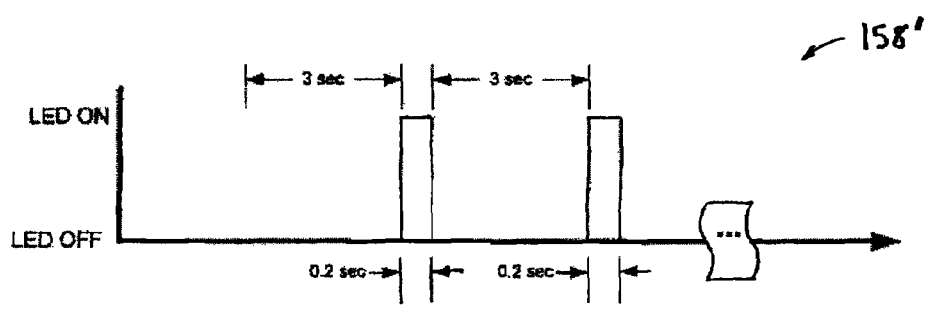
FIG. 7B is a chart that illustrates an LED indication sequence of the present embodiment that may be executed during a lockout mode of the operational procedure of FIGS. 4 and/or 5.
Figure 7C:
FIG. 7C is a chart that illustrates an LED indication sequence of the present embodiment that may be executed during an active mode of the operational procedure of FIGS. 4 and/or 5.

Referring now to FIGS. 7A-C, the energy efficient LED indication sequences of the present embodiment are illustrated. Similar to the prior art dispensers, in the present embodiment the controller operates the LED 110 to indicate to a user the operational state of the dispenser, i.e., the initiate mode 152, the active mode 156, the lockout mode 158, or the dispense mode 130. As shown in FIG. 7A, during a dispense mode operational state 130', the controller 102 causes the LED 110 to blink 4 times per second for 3 seconds. Specifically, the LED is powered on for 125 milliseconds and successively powered off for 125 milliseconds. This pattern is repeated 12 times. This rapid series of blinking provides a more noticeable indication to the user that the dispenser 120 has detected motion and is about to spray than the LED sequence of the indicated prior art dispenser. See, for example, FIG. 6A, which has a much slower series of blinking that is not as noticeable to a user. The power required to activate the LED 110 during the dispense mode 130' is 0.00125 mAh. In the present embodiment (see FIG. 7A), the LED 110 is not energized during the dispense mode 130A initiated by the depression of the pushbutton 116. The provision of an indication sequence during a manual actuation mode has been found to be unnecessary, because the user has initiated the activity and is therefore already aware that the dispenser is about to release material. However, it is contemplated that the controller 102 may power the LED 110 during the dispense mode operational state 130A according to the same LED sequence as during the dispense mode operational state 130'.

As shown in FIG. 7B, during a lockout mode 158' the controller 102 powers the LED 110 on every 3.2 seconds. Specifically, the LED 110 is off for a 3 second period and then powered on for a 0.2 second period. The on/off periods are repeated until the lockout time period X expires, e.g., after 20 minutes. It is beneficial to alternate powering the LED 110 on and off during the lockout mode 158' to inform the user that the dispenser 120 is still operating even though no dispense mode 130' is initiated when the user passes by the dispenser 120. The amount of power required to activate the LED 110 during the lockout mode 158' is 0.0625 mAh.

Referring to FIG. 7C, during an active mode 156' the LED 110 is turned off for the duration of the active mode 156', i.e., until the sensor 108 detects sensory input. The amount of energy consumed during 5 seconds of the active mode 156' is 0.000069 mAh. Turning the LED 110 off for the duration of the active mode 156' rather than pulsing the LED 110 on and off provides a clearer indication to the user that the dispenser 120 is in the active mode 156' and not the lockout mode 158'. Further, it is typically not necessary to use an LED indication sequence during the active mode 156' because the user is not often positioned in a manner to see the LED 110 during this period. When the user is in the vicinity of the dispenser 120 where the LED 110 is noticeable, the sensor 108 would have normally either detected the presence of the user and initiated the dispense mode of operation 130' and the accompanying rapid sequence of light blinking or will be in the lockout mode 158' with the accompanying slower sequence of light blinking. Such an LED indication sequence not only enhances energy consumption, but is more intuitive for user's to understand.

In the present embodiment, when the LED is powered on, the controller operates the LED 110 using a pulse width mode of operation preferably at a 20% to 100% duty cycle, more preferably at a 40% to 80% duty cycle, and most preferably at a 50% duty cycle. The controller operates the duty cycle preferably at an 80 to 200 hertz rate and most preferably at a 100 hertz rate. The pulse width mode of operation may be adjusted to save energy or change the brightness of the LED, while still powering the LED to appear continuously on. For clarity, the pulse width mode is not illustrated in the indication sequences illustrated in FIGS. 7A-7C.

A comparison of the energy consumption of the LED operational sequences for the dispense mode 130/130', lockout mode 158/158', and active mode 156/156', of the present embodiment are compared to the energy requirements of the LED sequences of the prior art dispensers in the following Table 1.

TABLE 1

| MODE | ENERGY REQUIREMENTS | |
| --- | --- | --- |
|  | Prior Art | Present Embodiment |
| Dispense Mode | 0.00125 mAh | 0.00125 mAh |
| Lockout Mode (20 min.) | 1.0000 mAh | 0.0625 mAh |

TABLE 1-continued

| MODE | ENERGY REQUIREMENTS | |
| --- | --- | --- |
|  | Prior Art | Present Embodiment |
| Active Mode (5 sec.) | 0.000486 mAh | 0.000069 mAh |
| Motor drive for 1 spray | 0.2368 mAh | 0.2368 mAh |

In some dispensers 120, power is supplied by the insertion of one or more batteries, e.g., 2-AA batteries 126, as discussed above. The energy efficient LED indication sequences of the present embodiment increase the lifetime of the power source, thereby allowing the dispenser 120 to operate using fewer batteries 126 over the lifetime of the dispenser 120. Specifically, the dispenser 120 can be operated using one or more batteries 126 having a preferred capacity rating of about 400 to about 4000 mAh. Alternatively, in another embodiment the dispenser 120 can be operated using one or more batteries 126 having a preferred capacity rating of about 400 to about 3000 mAh. Batteries such as these allow the dispenser to operate for at least 3 months of normal, continuous operation without replacing the batteries. In a preferred embodiment, the dispenser 120 is capable of operating with 2-AA batteries having a capacity rating of about 400 to about 3000 mAh for at least 5 months of continuous operation before the batteries need to be replaced. In another preferred embodiment, the dispenser 120 is capable of operating with 2-AA batteries having a capacity rating of about 400 to about 3000 mAh for at least 7 months of continuous operation before the batteries need to be replaced. Alternatively, in another preferred embodiment, the dispenser 120 is capable of operating with 2-AA batteries having a capacity rating of about 400 to about 4000 mAh for at least 5 months and/or at least 7 months of continuous operation before the batteries need to be replaced.

In one example, 2-AA alkaline batteries are used to provide power to the dispenser 120. In connection with the presently disclosed embodiment, the 2-AA alkaline batteries will last about 14 container refills 122. With typical consumer usage, a container refill 122 usually lasts for about 20 to about 30 days of normal operation of the dispenser 120. In fact, 2-AA alkaline batteries will last for preferably about 7 to about 24 months, more preferably about 10 to about 18 months, and most preferably 14 months of normal operational use of the dispenser 120. In the previously disclosed prior art dispenser discussed above, the same batteries would last for only 5-6 refills. As such, the life of batteries 126 used in dispensers operating according to the present LED indication sequences may be twice as long as the life of batteries 126 used in previously indicated prior art dispensers. Dispensers 120 operating with the present energy efficient LED sequences provide greater convenience to the user by requiring the replacement of batteries 126 less frequently. Additionally, the present dispensers 120 have lower operational costs over the lifetime of the dispenser due to fewer battery replacements. Further, regardless of the type of power source 104 used, the present dispenser 120 maximizes the lifetime of the power source 104 and overall uses less energy over the lifetime of the dispenser.

Although the indicator 110 of the present embodiment is described as being an LED it is contemplated that other types of indicators may be used to provide an indication to the user of the operational state of the dispenser. For example, the indicator may be another visual indicator such as a non-LED light or the indicator could be an audible indicator or a vibrational indicator.

It is also contemplated that other types of dispensers with varying actuation mechanics may be used in conjunction with any of the embodiments disclosed herein. For example, instead of using a dispenser capable of releasing spray bursts of various volumes from a single container it is possible to use a dispenser capable of releasing spray bursts from multiple containers with differently metered or non-metered valves. Also, instead of using a dispenser that uses a container with a metered valve, it is possible to use a dispenser that uses submetered valves, in which the submetering happens within the dispenser and not within the container. For example, it is contemplated that the dispenser may use an electronically controlled solenoid in combination with a container having a non-metered or metered valve to release various volumes of spray material from the dispenser.

It is further contemplated that any of the described dispensers could use a remote sensor as opposed to the sensor 108 located within the housing of the dispenser. Remote sensors have the advantage of allowing the dispenser 120 to detect sensory input that is not in the same location as the dispenser 120 or to increase the range of detection. Additionally, any of the described dispensers may use multiple sensors, located within or outside of the dispenser 120, to equip the dispenser with omni-directional detection capabilities.

It is also contemplated that any of the above embodiments may be modified to include a user selectable switch. The user selectable switch allows a user to choose a preferred lockout period time. Alternatively, instead of a switch, the dispenser could include a wheel or a dial, which the user can turn to select a preferred lockout period time or times.

Further, it has been contemplated that any of the improved indicating sequences may be used in conjunction with non-aerosol based dispensing systems. For example, similar active and/or lockout modes are found in connection with various dispensers that include activation mechanisms that activate pump-type valves, heat containers, heat wicks extending from or into a container, heat areas adjacent a wick and/or container, run a fan within a housing to assist in dispersal of a product, activate a piezo-electric plate adjacent a wick to volatize a fluid thereon, utilize a nebulizer or diffuser to disperse a product, open a window or otherwise remove an obstruction from an aperture or opening to assist in the dispersal of product from the housing, or otherwise effect dispersal of a product during a dispense mode from a container, reservoir or other product containing receptacle. Such fluids or volatiles include, but are not limited to, one or more of a pressurized fluid, a non-pressurized fluid, an oil, a candle, a wax melt, and a gel.

Those skilled in the art will appreciate the numerous variations that may be made with respect to the present disclosure and which are intended to be captured herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. An energy efficient dispenser for dispensing product from a container, comprising:
    a dispensation cycle consisting of an activation mechanism and three modes, which include an active mode that allows for dispensation, a lockout mode that does not allow for dispensation, and a dispensing mode that activates the activation mechanism,
    at least one indicator for displaying a first indication sequence when the dispenser is in a dispense mode operational state and a second indication sequence when the dispenser is in a lockout mode operational state,
    wherein each indication sequence comprises one or more activations of the at least one indicator, which utilize no more than 0.0625 mAh of energy to provide an indication to a user of the operational state of the dispenser.

2. The energy efficient dispenser of claim 1, wherein the at least one indicator is a light.

3. The energy efficient dispenser of claim 2, wherein the at least one indicator is an LED.

4. The energy efficient dispenser of claim 1, wherein the at least one indicator is an audible indicator.

5. The energy efficient dispenser of claim 1 further including at least one of a timer or a sensor for detecting sensory input, wherein the sensor includes one or more of a light sensing element, a passive infrared sensor, a motion sensor, an acoustic sensor, a humidity sensor, a temperature sensor, a pressure sensor, a vibration sensor, an accelerometer, a chemical sensor, and a mechanical contact switch.

6. The energy efficient dispenser of claim 5, wherein the sensor is activated during an active mode operational state to detect sensory input and the at least one indicator is powered off.

7. The energy efficient dispenser of claim 6, wherein upon the detection of sensory input the dispenser enters a dispense mode operational state, in which product is released from a container.

8. The energy efficient dispenser of claim 5, wherein the dispenser enters a dispense mode operational state upon the lapsing of a lockout period, in which product is released from a container.

9. An energy efficient dispenser for dispensing product from a container, comprising:
    at least one of a timer and a sensor; and
    at least one indicator for providing one or more indication sequences,
    wherein each indication sequence comprises one or more activations of the at least one indicator, which utilize no more than 0.0625 mAh of energy and operate using a pulse width mode of operation at a duty cycle of about 40% to about 80%, to provide an indication to a user of a plurality of operational states of the dispenser, and
    wherein the plurality of operational states includes at least:
    an active mode;
    a lockout mode; and
    wherein the active mode allows for dispensation of a product and the lockout mode does not allow for the dispensation of a product.

10. The energy efficient dispenser of claim 9, wherein the at least one indicator operates using a pulse width mode of operation at a duty cycle of about 50%.

11. The energy efficient dispenser of claim 10, wherein the duty cycle is operated at about 60 Hz to about 200 Hz.

12. The energy efficient dispenser of claim 9, wherein the at least one indicator is a light.

13. The energy efficient dispenser of claim 9, wherein the at least one indicator is an audible indicator.

14. The energy efficient dispenser of claim 9 further including at least one of a timer and a sensor for detecting sensory input, wherein the sensor includes one or more of a light sensing element, a passive infrared sensor, a motion sensor, an acoustic sensor, a humidity sensor, a temperature sensor, a pressure sensor, a vibration sensor, an accelerometer, a chemical sensor, and a mechanical contact switch.

15. An energy efficient dispenser, comprising:

a housing for receipt of a container and two or less batteries having a capacity rating of about 400 mAh to about 4000 mAh;

at least one of a timer and a sensor to detect sensory input; and at least one indicator for the provision of one or more indication sequences, wherein each indication sequence comprises one or more activations of the at least one indicator to provide an indication to a user of the operational state of the dispenser, wherein the two or less batteries are capable of providing power to the dispenser for at least seven months of continuous operation of the dispenser.

16. The energy efficient dispenser of claim 15, wherein the batteries are capable of providing power to the dispenser for at least a year of continuous operation of the dispenser.

17. The energy efficient dispenser of claim 15, wherein the at least one indicator is a visual indicator.

18. The energy efficient dispenser of claim 17, wherein the at least one indicator is an LED.

19. The energy efficient dispenser of claim 15, wherein the at least one indicator is an audible indicator.

20. The energy efficient dispenser of claim 15, wherein the at least one indicator is turned off during an active mode operational state, in which a sensor is activated; the at least one indicator is activated once every 3.2 seconds during a lockout mode operational state; and the at least one indicator is activated 4 times per second during a spray operational state, in which product is released from a container.

* * * * *